(12) United States Patent
Kawamura

(10) Patent No.: US 6,203,574 B1
(45) Date of Patent: Mar. 20, 2001

(54) PROSTHETIC BONE FILLER AND PROCESS FOR THE PRODUCTION OF THE SAME

(75) Inventor: Katsumi Kawamura, Tokyo (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/290,190

(22) Filed: Apr. 13, 1999

(30) Foreign Application Priority Data

Apr. 14, 1998 (JP) .................................................. 10-120139

(51) Int. Cl.⁷ .............................. A61F 2/28; A61F 5/00; B01D 15/08
(52) U.S. Cl. .................................... 623/16.11; 623/23.56; 623/23.58; 623/901; 501/82
(58) Field of Search .......................... 623/16, 901, 23.56, 623/23.58, 16.11; 501/82; 128/898

(56) References Cited

U.S. PATENT DOCUMENTS

| 4,149,894 | 4/1979 | Ebihara et al. . | |
|---|---|---|---|
| 4,230,455 | 10/1980 | Hidaka et al. . | |
| 4,777,153 | * 10/1988 | Sonupariak et al. | 501/82 |
| 4,842,603 | * 6/1989 | Draenert | 623/16 |
| 4,904,257 | 2/1990 | Mori et al. . | |
| 4,957,674 | 9/1990 | Ichitsuka et al. . | |
| 5,030,611 | 7/1991 | Ogawa et al. . | |
| 5,064,436 | 11/1991 | Ogiso et al. . | |
| 5,082,566 | 1/1992 | Tagaya et al. . | |
| 5,082,803 | 1/1992 | Sumita . | |
| 5,089,195 | 2/1992 | Ichitsuka et al. . | |
| 5,137,534 | 8/1992 | Sumita . | |
| 5,171,720 | 12/1992 | Kawakami . | |
| 5,338,772 | 8/1994 | Bauer et al. . | |
| 5,370,692 | * 12/1994 | Fink et al. | 623/16 |

FOREIGN PATENT DOCUMENTS

| 5237180 | 9/1993 | (JP) . |
|---|---|---|
| 7-8547 | 1/1995 | (JP) . |
| 10-52485 | 2/1998 | (JP) . |

* cited by examiner

Primary Examiner—Vincent Millin
Assistant Examiner—Choon P. Koh
(74) Attorney, Agent, or Firm—Greenblum & Bernstein, P.L.C.

(57) ABSTRACT

A prosthetic bone filler including ceramic granules for use in a living body, the ceramic granules being bonded to each other with a polymeric substance, and having ventilation pores produced as a result of the presence of gaps between the adjacent granules. The prosthetic bone filler is produced by adding the polymeric substance in two portions to the ceramic granules. In addition to good flexibility, the prosthetic bone filler exhibits excellent bio-compatibility.

13 Claims, 1 Drawing Sheet

PROSTHETIC BONE FILLER AND PROCESS FOR THE PRODUCTION OF THE SAME

BACKGROUND OF THE INVENTION

1. Field of the Invention

The present invention relates to a prosthetic bone filler and a process for the production of the same.

2. Description of the Related Art

Recently, when a lacking site was produced in a bone due to bone diseases, injury and other causes, an artificial prosthetic material or prosthetic filler is embedded in the lacking site of the bone. The lacking sites of the bone to which the prosthetic filler is applied include a wide variety of bone sites such as cranium, vertebra and articulate. Furthermore, the materials used as a prosthetic filler include ceramic materials such as alumina or hydroxyapatite, metallic materials such as Ti or Co—Cr alloy, and resinous materials such as polymethyl methacrylate or high density polyethylene. Among these prosthetic fillers, the fillers made of alumina, hydroxyapatite and other ceramic materials have less flexibility than the bone itself, because they are solely made from the ceramic material. Due to less flexibility when only a small amount of bone surrounds the site in which the ceramic filler is embedded, the bone surrounding the filler can be sometimes destroyed when an external mechanical force or load is applied to the body having the embedded filler. To solve this problem, use of the prosthetic filler produced by mixing a ceramic material with a resinous material has been proposed. For example, Japanese Unexamined Patent Publication (Kokai) No. 5-237180 discloses a bone bonding device including a core material, produced upon extrusion molding of a mixture of hydroxyapatite, a biologically degradable polymer, and a melt-molded coating of polylactic acid. However, due to lack of porosity, the bone bonding device does not exhibit ventilation properties, and hence, lacks bio-compatibility. Further, Japanese Unexamined Patent Publication No. 7-8547 discloses a prosthetic filler including a porous block of sintered calcium phosphate compound having impregnated in an inner and surface portion thereof a biologically absorbing polymeric substance. However, the prosthetic filler also does not exhibit bio-compatibility; and the mechanical characteristics substantially depend upon the ceramic material used, i.e., a calcium phosphate compound instead of a polymeric substance.

SUMMARY OF THE INVENTION

It is an object of the present invention to provide a prosthetic bone filler having excellent bio-compatibility, and good flexibility.

Another object of the present invention is to provide a production process suitable for the production of such a prosthetic bone filler.

In an aspect of the present invention, there is provided a prosthetic bone filler which includes ceramic granules for use in a living body, the ceramic granules being bonded to each other with a polymeric substance, and having ventilation pores produced due to gaps between the adjacent the ceramic granules.

Preferably, the polymeric substance bonding the ceramic granules includes finely divided ceramic particles having a particle size smaller than that of the ceramic granules.

Preferably, the polymeric substance is able to be absorbed in a living body.

According to another aspect of the present invention, there is provided a production process for a prosthetic bone filler including ceramic granules for use in a living body, the ceramic granules being bonded to each other with a polymeric substance, and having ventilation pores produced due to gaps between the adjacent granules. The production process includes: adding the polymeric substance to the ceramic granules in portions, after the polymeric substance is divided into two portions, in a bonding process of the ceramic granules with the polymeric substance.

Preferably, the polymeric substance added as the first portion to the ceramic granules is mixed with the ceramic granules after heating to make the ceramic granules adhesive; subsequently the polymeric substance is added as the second portion in the form of solid particles to the ceramic granules; and subsequently the ceramic granules are heated after being mixed with the polymeric substance.

Preferably, the polymeric substance as the first portion has a particle size of less than one half of the maximum particle size of the ceramic granules, and the polymeric substance as the second portion has a particle size of at least twice the minimum particle size of the ceramic granules.

Preferably, finely divided ceramic particles having a particle size smaller than the ceramic granules to be bonded with the polymeric substance are further added to the polymeric substance as the second portion.

The present disclosure relates to subject matter contained in Japanese Patent Application No.10-120139 (filed on Apr. 14, 1998) which is expressly incorporated herein by reference in its entirety.

DESCRIPTION OF THE PREFERRED EMBODIMENTS

Figure 1:
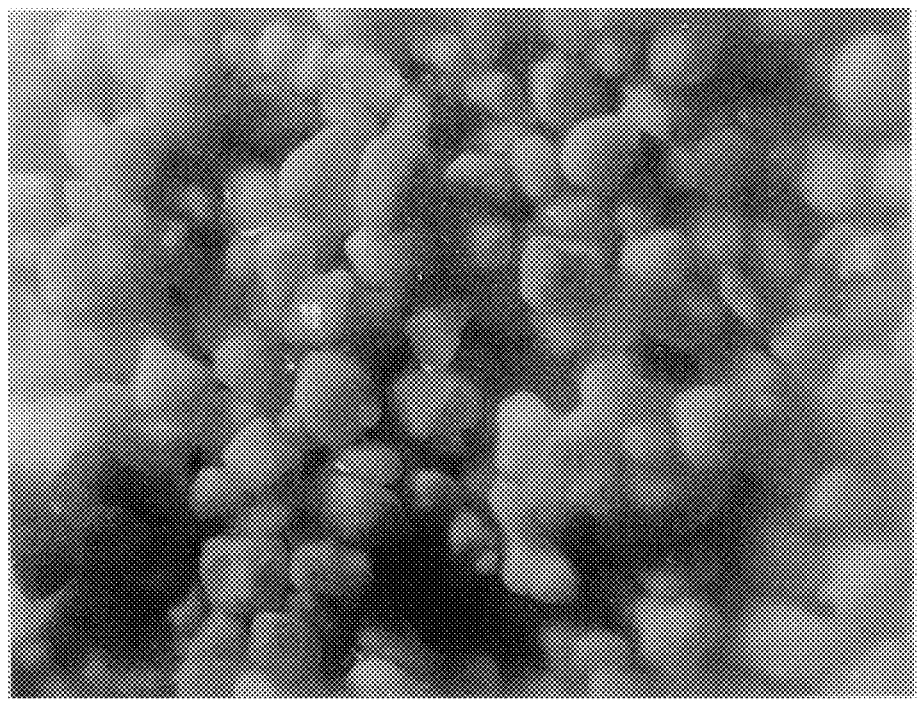
FIG. 1 is a microphotograph of a cross section of the porous body produced in Example 1 taken at a magnification of 26 times by an optical microscope.

As described above, the prosthetic bone filler includes ceramic granules designed for use in a living body, the ceramic granules being bonded to each other with a polymeric substance, and having ventilation pores or cells produced as a result of the presence of gaps between the adjacent granules.

In the prosthetic bone filler, the ceramics used herein include alumina, calcium phosphate compound, zirconia. These ceramics may be used alone or as a combination of two or more thereof. The calcium phosphate compound can be advantageously used among the above ceramics due to the bio-compatibility thereof.

A calcium phosphate compound having a molar Ca/P ratio of about 1.0 to 2.0 may be used as the calcium phosphate compound. Typical examples thereof include hydroxyapatite, tricalcium phosphate, tetracalcium phosphate, and calcium hydrogenphosphate. These calcium phosphate compounds may be used alone or as a combination of two or more thereof.

Although the temperature of a thermal treatment may be varied depending upon the types of the ceramics used, when the calcium phosphate compound is used, a thermal treatment at a temperature of about 700 to 1,200° C. is preferably applied to the calcium phosphate compound.

Furthermore, although it is not specifically limited, a particle size of the ceramic granules for use in a living body is generally preferred to be in the range of about 10 to 1,000 $\mu$m. The particle size of the ceramic granules of less than 10 $\mu$m may cause a rejection reaction of the living body with a foreign substance, and the particle size of more than 1,000 $\mu$m may cause a reduction of the strength of the resulting porous body as a result of reduction of the number of the bonded ceramic granules.

The polymeric substance used as a binder for bonding the ceramic granules is not specifically restricted, as long as it can be suitably used in a living body, and includes both polymeric substances capable and incapable of being absorbed in a living body. Typical examples of polymeric substance incapable of being absorbed in a living body include polymethyl methacrylate, high density polyethylene and polytetrafluoroethylene. Typical examples of polymeric substances capable of being absorbed in a living body include synthetic substances such as poly ε-caprolactone, polylactic acid, polyglycolic acid and their copolymers, and naturally occurring substances such as fibrin, collagen and chitin.

In addition, it is preferred in order to obtain good bio-compatibility, the polymeric substance bonding the ceramic granules contains, at least in part, ceramic particles having a particle size smaller than that of the ceramic granules.

In the production of the prosthetic bone filler according to the present invention, in order to bond each ceramic granule for use in a living body with the polymeric substance, the polymeric substance is added to the ceramic granules after being divided into two portions. If the desired amount of polymeric substance is added all at once, the molecules of the polymeric substance would adhere to each other, and hence, would not bond properly with the ceramic granules; for this reason, the polymeric substance is added in two portions. In the first and second addition steps of the polymeric substance, the same or different polymeric substances may be used.

In the above-mentioned addition of the polymeric substance to the ceramic granules, a blending ratio of the polymeric substance to the ceramic granules in the first addition step is preferred to be in the range of about 0.05 to 1.0 in terms of a volume ratio of the polymeric substance per ceramic granule. A volume ratio of the polymeric substance per ceramic granule in the first addition step of less than 0.05 may cause a problem with the added polymeric substance not being able to extend over all of the ceramic granules. A volume ratio of more than 1.0 may cause the surface of the ceramic granules can be fully covered with the added polymeric substance, thereby preventing good bio-compatibility.

In the second addition step, a blending ratio of the polymeric substance to the ceramic granules is preferred to be in the range of about 0.1 to 1.4 in terms of a volume ratio of the polymeric substance per ceramic granule. A volume ratio of the polymeric substance per ceramic granule in the second addition step of less than 0.1 may cause a problem with the added polymeric substance not being able to extend over all of the ceramic granules. A volume ratio of more than 1.4 may cause a problem with ventilation properties being lost from the resulting molded product. In other words, good affinity (which depends on the porosity) of the ceramic granules is lost from the molded product.

In the production process, it is preferred that the polymeric substance to be added in the first addition step is heated to make it adhesive, followed by adding the resulting adhesive substance to the ceramic granules, and the polymeric substance to be added in the second addition step is added in the form of solid particles to the ceramic granules, which have been mixed with the ceramic granules in the first addition step, followed by mixing and heating.

Moreover, it is also preferred that the ceramic granules used are previously heated to a predetermined temperature in order to prevent solidification of the polymeric substance, because in the first addition step, the adhesive polymeric substance produced upon heating can be suddenly cooled when it is contacted with the ceramic granules during the mixing thereof with the ceramic granules.

The size of the particles of the polymeric substance added to the ceramic granules can affect ventilation and strength of the resulting porous body.

More particularly, it is preferred that the particulate polymeric substance to be added to the ceramic granules in the first addition step has a particle size of not more than about one half of the maximum particle size of the ceramic granules, and the particulate polymeric substance to be added in the second addition step has a particle size of not less than about twice the minimum particle size of the ceramic granules. The particle size of the first added polymeric substance of more than one half of the maximum particle size of the ceramic granules may cause a problem with the added polymeric substance not being able to uniformly adhere to the surface of the ceramic granules. Furthermore, the particle size of the second added polymeric substance of less than twice the minimum particle size of the ceramic granules may cause a problem with the added polymeric substance completely filling the gaps of the ceramic granules, thereby resulting in the prosthetic bone filler having no ventilation properties.

In addition, with regard to the polymeric substance to be added in the second addition step, if finely divided ceramic particles having a particle size smaller than that of the ceramic granules to be bonded with the polymeric substance are further added to the second added polymeric substance, it becomes possible to improve the bio-compatibility of the resulting layer of the polymeric substance, and thus, improving the entire bio-compatibility of the resulting prosthetic bone filler. In this case, the finely divided ceramic particles are preferably added to the second added polymeric substance in an amount sufficient to ensure that the volume of the (added) finely divided ceramic particles occupy about 25% to 50% based on a total amount of the second added polymeric substance and finely divided ceramic particles. A volume of ceramic particles of less than 25% may cause a problem with a large amount of the ceramic particles added being embedded in the polymeric substance so that the desired improvement of affinity cannot be obtained. Furthermore, more than 50% of the volume of the ceramic particles may cause insufficient bonding of the ceramic granules by the polymeric substance.

THE EMBODIMENT

The present invention will be further described with reference to the working examples thereof. Note, however, that the present invention should not be restricted to these examples.

Hydroxyapatite was prepared in a wet process in accordance with a coprecipitation method, and was spray dried to obtain hydroxyapatite granules having an average particle size of 100 $\mu$m. The hydroxyapatite granules and demineralized water were mixed at a mixing ratio by weight of 1:3, and the mixture was poured into a mold. After drying, the hydroxyapatite mold was milled in a milling machine to obtain hydroxyapatite granules having a particle size of about 10 to 5,000 $\mu$m. The hydroxyapatite granules were then heated at a rate of 100° C. per hour to 1,200° C., and thereafter were maintained at the same temperature for 4 hours. Thereafter, the heated hydroxyapatite granules were cooled at a rate of 100° C. per hour until reaching room temperature. After thermal treatment of the hydroxyapatite granules was applied in the above-described manner, the hydroxyapatite granules were sieved to obtain hydroxyapatite granules having a particle size of 100 to 300 $\mu$m.

Polylactic acid commercially available under the trade name "LACTY" from Shimazu Seisakusho Co., Ltd., was milled in a milling machine to obtain polylactic acid particles having a particle size of 50 to 2,000 $\mu$m. The polylactic acid particles were then classified into those having a particle size of less than 210 $\mu$m and those having a particle size of 210 to 420 $\mu$m. The obtained polylactic acid particles having a particle size of 210 to 420 $\mu$m were further mixed with fine hydroxyapatite particles having a particle size of 10 to 30 $\mu$m at a ratio by volume of 3:1 (polylactic acid : hydroxyapatite).

Next, the hydroxyapatite granules having a particle size of 100 to 300 $\mu$m (hereinafter, referred also to "HAP") were heated to 200° C. and maintained at 200° C. for one hour, while the polylactic acid particles having a particle size of not more than 210 $\mu$m were heated to 100° C. and maintained at 100° C. for one hour. Subsequently, the heated HAP granules were added to a container containing the heated polylactic acid particles at a mixing ratio by volume of 0.25 (polylactic acid/HAP granules), followed by the container being intensely shaken to mix the polylactic acid particles with the HAP granules. The polylactic acid particles were thus adhered to a surface of the HAP granules.

After the HAP granules coated with the polylactic acid particles were cooled to a temperature of not more than 100° C., the previously prepared mixture of the polylactic acid particles having a particle size of 210 to 420 $\mu$m with the fine hydroxyapatite particles having a particle size of 10 to 30 $\mu$m was added to a container containing the polylactic acid particles-coated HAP granules at a mixing ratio by volume of 0.28 (polylactic acid/HAP granules exclusive of fine HAP particles), followed by the container being intensely shaken to mix the polylactic acid particles with the HAP granules and the fine HAP particles. The resulting mixture was poured into a mold, heated to 195° C., and maintained the same temperature for two hours. The molded product was then left to stand under natural cooling conditions.

Subsequently, a porous molded body of hydroxyapatite having ventilation properties was thus obtained. The porous molded body was mechanically fabricated to obtain a test sample in the form of a rectangular parallelopiped having a size of 2 mm×5 mm×5 mm. After a pressure difference of 750 mmHg was applied to a lower surface of the test sample to generate a negative pressure thereon, demineralized water was added in drops to the upper surface of the test sample to determine an amount of water permeated through the test sample per minute. The determined amount of water of 29 mL showed that the porous molded body of hydroxyapatite has good ventilation properties.

To confirm the bonding state of the HAP granules in the porous molded body of hydroxyapatite, a microphotograph of the cross section was taken at a magnification of 26 times by an optical microscope. The microphotograph is shown in FIG. 1.

As can be understood from the above descriptions, according to the production process of the prosthetic bone filler according to the present invention, a highly efficient porous prosthetic bone filler has been achieved in which the ceramic granules as the material for use in a living body are bonded to each other with a polymeric substance, while retaining pores or cells between the bonded granules.

Furthermore, since the ceramic granules are bonded to each other with a polymeric substance, while retaining pores between the granules, the prosthetic bone filler of the present invention exhibits an excellent bio-compatibility, in addition to good strength and ventilation properties, and also exhibits a higher flexibility in comparison to a prosthetic bone filler consisting of only a ceramic material. The prosthetic bone filler of the present invention can exhibit excellent bio-compatibility especially when the polymeric substance bonding the ceramic granules contains, at least in part, finely divided ceramic particles having a particle size smaller than that of the ceramic granules. Furthermore, when a polymeric substance capable of being absorbed in a living body is used as the polymeric substance, the corresponding portion in the resulting prosthetic bone filler can be substituted with an osseous tissue of the bone.

Although the invention has been described with reference to particular means, materials and an embodiment, it is to be understood that the present invention is not limited to the particulars disclosed and extends to all equivalents within the scope of the claims.

What is claimed is:

1. A prosthetic bone filler for use in a living body, comprising ceramic granules, polymeric substance bonding said ceramic granules to each other, and ventilation pores produced due to gaps between the bonded ceramic granules.

2. The prosthetic bone filler according to claim 1, wherein said polymeric substance bonding said ceramic granules comprises finely divided ceramic particles having a particle size smaller than that of said ceramic granules.

3. The prosthetic bone filler according to claim 1, wherein said polymeric substance is able to be absorbed in a living body.

4. The prosthetic bone filler according to claim 1, wherein the particle size of said ceramic granules is within a range of 10 $\mu$m to 1000 $\mu$m.

5. A production process for a prosthetic bone filler for use in a living body, comprising ceramic granules, polymeric substance bonding said ceramic granules to each other, and ventilation pores produced due to gaps between the bonded ceramic granules, said production process comprising:

adding the polymeric substance to the ceramic granules in plural portions of said polymeric substance so that the polymeric substance bonds the ceramic granules to each other with ventilation pores produced due to gaps between the bonded ceramic granules.

6. The production process according to claim 5, wherein said polymeric substance is added as a first portion to said ceramic granules and is mixed with the ceramic granules after the polymeric substance is heated to make said ceramic granules adhesive; said polymeric substance is subsequently added as a second portion in the form of solid particles to the ceramic granules which has been made adhesive; and subsequently the ceramic granules are heated after being mixed with the second portion of the polymeric substance.

7. The production process according to claim 5, wherein said polymeric substance being added as a first portion has a particle size of less than one half of a maximum particle size of the ceramic granules, and the polymeric substance being added as a second portion has a particle size of at least twice a minimum particle size of the ceramic granules.

8. The production process according to claim 5, wherein the plural portions of polymeric substance comprise a first portion of polymeric substance and a second portion of polymeric substance, and finely divided ceramic particles having a particle size smaller than the ceramic granules to be bonded with the polymeric substance are added as the second portion of polymeric substance.

9. The production process according to claim 5, wherein the plural portions of said polymeric substance comprise a polymeric substance that has been divided into two portions.

10. The production process according to claim 6, wherein the first portion of polymeric substance is added in a volume ratio of the polymeric substance per ceramic granule in a range of about 0.05 to 1.0.

11. The production process according to claim 10, wherein the second portion of polymeric substance is added in a volume ratio of the polymeric substance per ceramic granule in a range of about 0.1 to 1.4.

12. The production process according to claim 6, wherein the second portion of polymeric substance is added in a volume ratio of the polymeric substance per ceramic granule in a range of about 0.1 to 1.4.

13. The production process according to claim 5, wherein the polymeric substance is able to be absorbed in a living body.

* * * * *